(12) United States Patent
Brenneman

(10) Patent No.: US 7,820,107 B2
(45) Date of Patent: Oct. 26, 2010

(54) OPTICAL REAGENTS FORMAT FOR SMALL SAMPLE VOLUMES

(75) Inventor: Allen J. Brenneman, Goshen, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 1216 days.

(21) Appl. No.: 10/694,376

(22) Filed: Oct. 27, 2003

(65) Prior Publication Data
US 2004/0091394 A1    May 13, 2004

Related U.S. Application Data

(60) Provisional application No. 60/421,641, filed on Oct. 29, 2002.

(51) Int. Cl.
*G01N 21/00* (2006.01)
*G01N 31/22* (2006.01)
*G02B 6/00* (2006.01)
*G01N 21/01* (2006.01)
*G01N 15/06* (2006.01)

(52) U.S. Cl. .................. 422/82.11; 422/55; 422/58; 422/68.1; 422/82.05; 422/82.06; 422/82.07; 422/82.08; 422/82.09; 385/12

(58) Field of Classification Search ............. 422/58, 422/82.06, 82.11; 385/132, 12
See application file for complete search history.

(56) References Cited

U.S. PATENT DOCUMENTS

| 4,803,992 A | * | 2/1989 | Lemelson | 600/342 |
| 5,264,702 A | * | 11/1993 | Mihalczo | 250/390.11 |
| 5,525,518 A | * | 6/1996 | Lundsgaard et al. | 436/68 |
| 6,001,307 A | * | 12/1999 | Naka et al. | 422/81 |

FOREIGN PATENT DOCUMENTS

| EP | 0 254 246 A2 | 1/1988 |
| WO | WO 88/01376 | 2/1988 |

OTHER PUBLICATIONS

Madow, *Fundamentals of Microfabrication* (CRC Publication) ISB:0-8493-9451-1 1997.

* cited by examiner

*Primary Examiner*—Jill Warden
*Assistant Examiner*—Neil Turk
(74) *Attorney, Agent, or Firm*—Nixon Peabody LLP

(57) ABSTRACT

An optical waveguiding optical format enables consistent optical analysis of small sample volumes with minimal variation in light path length among optical formats. The optical format is comprised of an input guide, an output guide, and a sample cavity adapted to allow light to pass through a sample on its way from the input guide to the output guide. A lid removed from the light pathway within the format may be provided with a reagent for assisting fluid analysis.

25 Claims, 3 Drawing Sheets

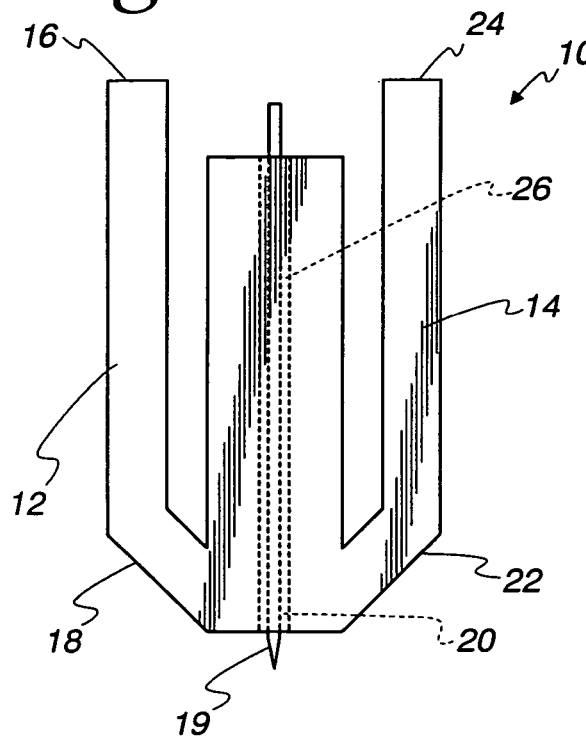
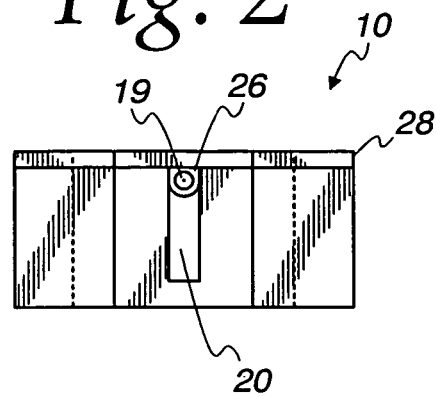
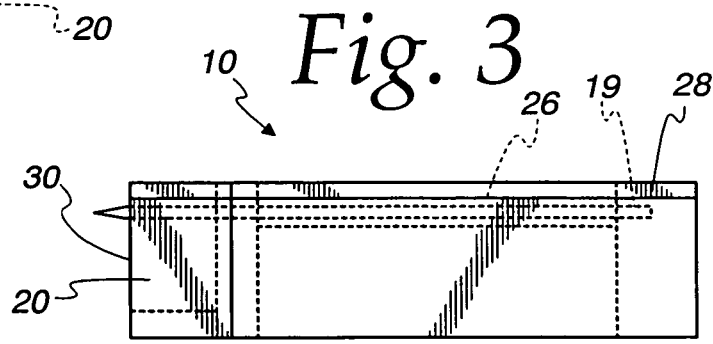
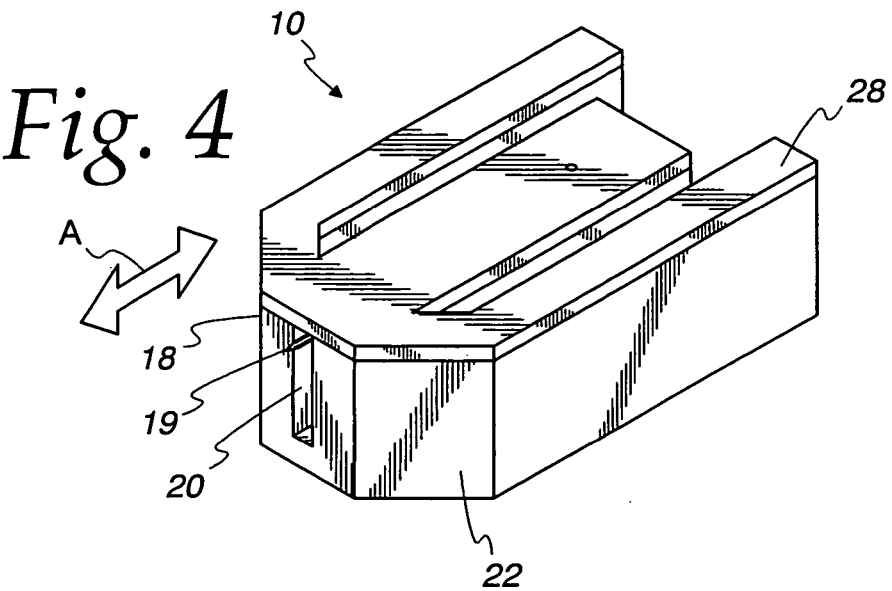

OPTICAL REAGENTS FORMAT FOR SMALL SAMPLE VOLUMES

CROSS-REFERENCE TO RELATED APPLICATION

This application claims benefit to U.S. Provisional Application No. 60/421,641, filed on Oct. 29, 2002

FIELD OF THE INVENTION

The present invention relates generally to medical testing and more specifically to an improved format for optical testing of fluids.

BACKGROUND OF THE INVENTION

Optical testing of samples has become increasingly popular in recent years due to the speed, accuracy, and efficiency with which test results can be acquired through optical testing. Because of these benefits, optical testing is commonly used in medical applications such as glucose testing. Generally, optical testing in medical applications involves passing light through a sample. In some applications, the sample may be combined with a reagent for testing. Upon passing through the sample or the combined sample and reagent, the test light is altered based on the qualities of the sample or sample/reagent combination. The light which passes through the sample comprises a detection beam which is input into a detector for analysis. Optical testing may employ "formats," objects upon which a sample may be collected and which allow for easy transport and testing of a sample.

Several problems arise in optical testing applications. One common problem is the contamination of equipment optics when a sample is input for analysis. Such contamination may require error detection for contaminated optics and/or major cleaning procedures for the user, and further results in overall contamination of an analysis instrument. Such contamination may result, for example, from a close proximity of a light source or light detector to the sample application area of a format. Further, in applications using optical formats (i.e., testing formats with optical components through which light travels), the variation of the length of the path through which light travels can lead to variable testing accuracy. Optical formats often incorporate lids that are within the light path, which can add to the variability of light path length. Additionally, when testing particularly small sample volumes, it is desirable to use a short path length and further to eliminate the need for any path length variation technique in the testing instrument. Other problems that arise in the use of formats for optical testing include the need for optimization of reagent deposition into the format and the need for a separate format and a device, such as a needle or lancet, for placing a sample into the format.

In order to increase the efficiency and accuracy of optical sample testing, it is desirable to reduce or eliminate these known problems.

SUMMARY OF THE INVENTION

According to one embodiment of the present invention, an optical format isolates source and detection optics from a sample application area using a molded plastic light pipe.

According to another embodiment of the present invention, an optical format is provided with a light pipe which guides input light through a sample and guides the resulting detection light back toward a detector.

According to another embodiment of the present invention, an optical format including a light pipe for guiding light through a sample is further provided with a lid at an angle to the sample such that the lid is not within the light path within the sample.

According to another embodiment of the present invention, a microfabricated optical format is provided with a short path length and allows for minimal path length variation between individual formats.

According to yet another embodiment of the present invention, a format design including several options for reagent deposition into the format is provided.

According to still another embodiment of the present invention, an optical format having a wave guide is provided with an integrated lancet needle.

BRIEF DESCRIPTION OF THE DRAWINGS

FIG. 1 is a top view of an optical format according to the present invention;

FIG. 2 is a front view of an optical format according to the present invention;

FIG. 3 is a side view of an optical format according to the present invention;

FIG. 4 is an isometric view of an optical format according to the present invention;

Figure 5:
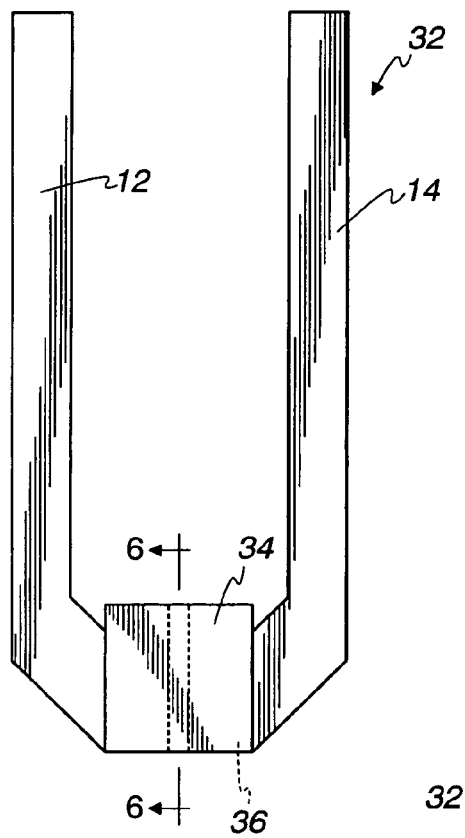
FIG. 5 is a top view of an alternative optical format according to the present invention.

While the invention is susceptible to various modifications and alternative forms, specific embodiments are shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DESCRIPTION OF SPECIFIC EMBODIMENTS

FIG. 1 shows an optical format 10 according to the present invention. The optical format 10 may be used in the collection and optical testing of samples, for example in medical testing applications such as glucose testing. The optical format 10 may be created using a variety of fabrication techniques, described more fully below, and may be constructed of such materials as polycarbonate, polystyrene or other plastics having the proper optical transmission characteristics.

An optical format 10 according to the present invention is provided with an input light guide 12 and an output light guide 14. The light guides could alternatively be considered "waveguides" or "light pipes." The input light guide 12 guides light from a light input 16 toward an input reflector 18. The input reflector 18 reflects the light through a sample cavity 20, where the light interacts with a sample or a combination of sample and reagent. For example, reagents that allow glucose measurements may be used. From the sample cavity 20, the light continues toward an output light reflector 22. The output reflector 22 reflects light through the output light guide 14, which guides the light to a light output 24 where it then enters the detection optics in the meter (not shown). According to one embodiment of the present invention, the optical format 10 is further provided with a venting channel 26, which works either with or without a lancet to allow venting or vacuuming of the sample cavity 20. According to one embodiment of the present invention 10, the input reflector 18 and output reflector 22 utilize total internal reflection to guide light respectively toward and away from the sample cavity 20. The surfaces of one or both of the input reflector 18 and output reflector 22 may be provided with reflective coatings.

The optical format 10 is designed to be mounted in an analyzing instrument (not shown) and aligned with source and detection optics. In the embodiment shown in FIG. 1, the input reflector 18 is disposed at a 45-degree angle to the input light guide 12 and the output reflector 22 is disposed at a 45-degree angle to the output light guide 14, though greater or lesser angles are contemplated depending on the specific application for the format 10. The optical format 10 allows for the isolation of light source optics and light detection optics (not shown) from the sample cavity 20. According to one embodiment of the optical format 10, the input light guide 12 and output light guide 14 are of sufficient length to allow a sample to be kept outside of an instrument for optical measurement of the sample.

Turning now to FIG. 2, a front view of the optical format 10 is shown, more clearly illustrating the structure of one embodiment of the sample cavity 20. The sample cavity 20 is shown in contact with the venting channel 26. Also visible in FIG. 2 is a full lid 28, which covers one surface of the optical format 10. The full lid 28 is beneficial in applications utilizing a reagent deposited on the lid 28 prior to lamination of the lid to a surface of the optical format 10. Further, it is to be noted that the lid 28 is parallel to the direction of light travel through the sample cavity 20 and does not constitute a portion of the light travel path. Depending on the application, it may be beneficial to provide a lid disposed at alternative angles to the direction of light travel, or covering the sample cavity 20 from different directions.

As can be seen more clearly in FIG. 3, the sample cavity 20 extends inwardly from a sample-side surface 30 of the optical format 10. FIG. 4 shows an isometric view of the optical format 10, further illustrating the relationships of its individual portions.

In use, the sample cavity 20 serves as a capillary gap for a cuvette-type cell holding a sample. During sample collection, sample-side surface 30 of the optical format 10 may be placed against the skin, with a lancet 19 placed through the venting channel 26. The lancet 19 may be moved relative to the format 10 in the directions shown by arrow "A" of FIG. 4. The lancet is provided to pierce the skin and further to apply a vacuum to the flesh after lancing. It is to be understood that each embodiment of a format according to the present invention may be provided with or without a lancet depending on particular format applications. The fluid sample is thus drawn or wicked into the sample cavity 20 where it may interact with a reagent provided on the lid 28. Once the sample has been acquired, a light source (not shown) directs light into the light input 16, and a transmission reading is taken at a given wavelength or wavelengths after the light has passed through the sample. These results may be analyzed or converted to a reading corresponding to the amount or concentration of glucose or other analyte of interest, and this reading may be displayed to the user. Following use of an optical format according to the present invention, the optical format may be discarded.

The present invention allows for several methods of application of a reagent into an optical format. In addition to providing a reagent on the lid 28 before construction of an optical format, other methods of providing a reagent may be used. For example, reagent may be deposited into the sample cavity 20 before the optical format 10 is fully assembled or it may be wicked into the optical format 10 after the format is assembled and dried.

Figure 6:
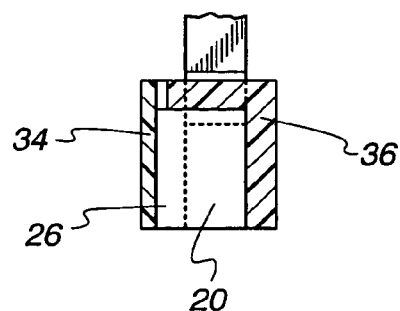
FIG. 6 is a cross-sectional view of the section defined by the line 6-6 in FIG. 5.
Figure 7:
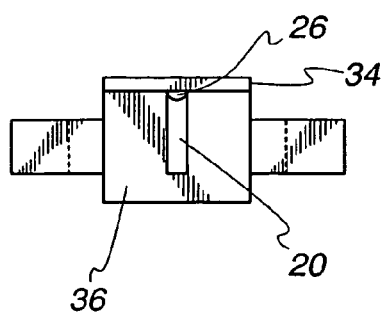
FIG. 7 is a front view of an alternative optical format according to the present invention.
Figure 8:
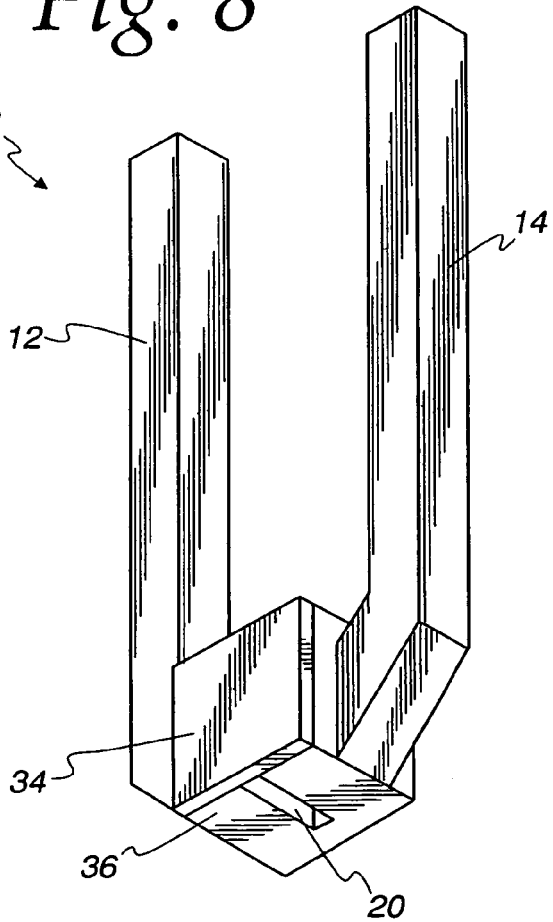
FIG. 8 is a perspective view of an alternative optical format according to the present invention.

Turning now to FIGS. 5-8, an alternative embodiment of an optical format (optical format 32) according to the present invention is shown. FIG. 5 is a top view of the optical format 32, and FIG. 6 is a cross-sectional view along the line "6-6" of FIG. 5. FIG. 7 is a front view of the optical format 32 and FIG. 8 is an isometric view of the optical format 32. The primary difference between the optical format 32 of FIGS. 5-8 is the use of a shorter lid 34 and a light transmission segment 36 which extends beyond the dimensions of the input light guide 12 and output light guide 14. This design allows the conservation of materials in the light guide portions as compared to the light transmission segment 36, which may be provided with greater dimensions to accommodate a lancet (not shown), the lid 34, and a reagent (not shown) and further to allow room for sample to be input into the sample cavity 20. In addition, this design reduces the amount of light that is lost when the light passes through the non-sample portion of the transmission segment 36. The lid 34 may be printed with a reagent, or a reagent may be provided on the lid via alternative methods such as screen printing, microdeposition, pin deposition, or as a matrix label containing the reagent.

Figure 9:
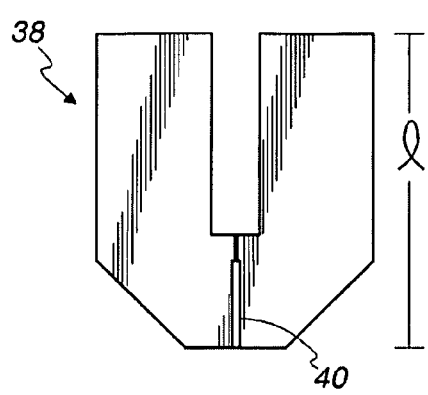
FIG. 9 is a top view of another alternative optical format according to the present invention.
Figure 10:
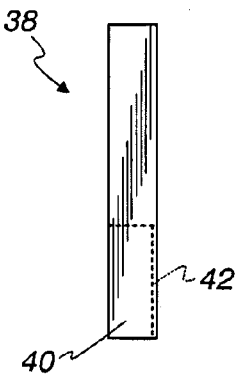
FIG. 10 is a side view of another alternative optical format according to the present invention.

Turning now to FIG. 9, an alternative embodiment of an optical format 38 is shown. The optical format 38 of this embodiment is provided without a lid. FIG. 9 shows a top view of an optical format 38 having a sample cavity 40 provided therein. FIG. 10 shows a side view of the optical format 38 and illustrates that the sample cavity 40 is bounded along side by cavity base 42. According to one embodiment, the cavity base 42 is integral with the remainder of hte optical format 38.

Figure 11:
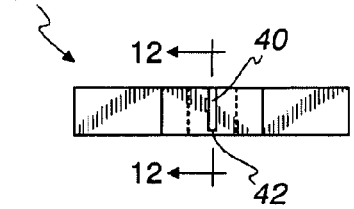
FIG. 11 is a front view of another alternative optical format according to the present invention.
Figure 12:
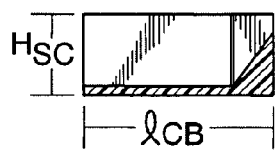
FIG. 12 is a cross-sectional view of the section defined by the line 12-12 in FIG. 11.

Turning now to FIG. 11, a front view of the optical format 38 is shown, further illustrating the relationship between the sample cavity 40 and the cavity base 42. FIG. 12 shows a cutaway view along the line "12-12" of FIG. 11 and further shows the dimensions of one embodiment of a sample cavity 40 according to the present invention. According to this embodiment, the cavity base 42 has a length, $l_{CB}$, of about 0.70 inches, and the sample cavity 40 has a height, $h_{SC}$, of about 0.035 inches, though it is contemplated that greater or lesser dimensions could be formed based on particular applications.

Figure 13:
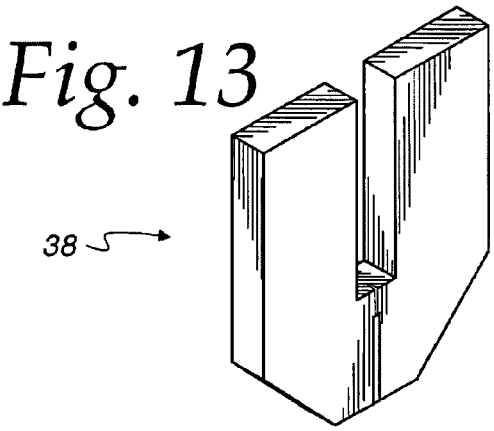
FIG. 13 is an isometric view of another alternative optical format according to the present invention.
Figure 14:
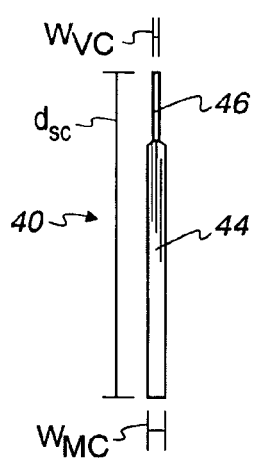
FIG. 14 is a front view of a sample cavity according to one embodiment of the present invention.
Figure 15:
FIG. 15 is a side view of a sample cavity according to one embodiment of the present invention.
Figure 16:
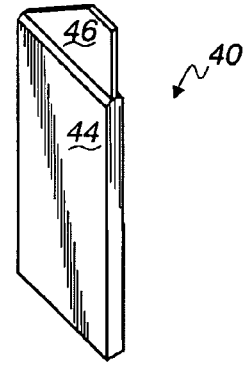
FIG. 16 is an isometric view of a sample cavity according to one embodiment of the present invention.

FIG. 13 is an isometric view of the optical format 38, more clearly showing the location of the sample cavity 40 in relation to the other portions of the optical format. FIG. 14 is a front view of the sample cavity 40, showing the width, $W_{MC}$, of a main cavity portion 44 and further showing the width, $W_{VC}$, of a venting cavity 46. According to one embodiment of the optical format 38, the width, $W_{MC}$, of the main cavity portion 44 is approximately 0.005 inches and the width, $W_{VC}$, of the venting cavity 46 is approximately 0.002 inches, though it is to be understood that wider or narrower spacing may be used based on specific applications of the optical format 38. FIGS. 15 and 16, respectively, are a side view and an isometric view of the sample cavity. According to one embodiment, the sample cavity 40 has a depth, $d_{sc}$, of about 0.035 inches.

An optical format according to the present invention may be fabricated using a variety of techniques, including microfabrication techniques, which can replicate multiple tool cavities without any significant variations from product to product. One example of a microfabrication technique which may be used to create an optical format according to the present invention is the LIGA process. The LIGA process is named after a German acronym and uses X-ray deep-etch lithography and electroplating and molding to create small formations having significant differences between height and depth measurements, or high "aspect ratios." Utilizing a microfabrication process, path length variation tolerance—that is, the difference in the distance of light travel in different optical formats—can be kept within an acceptable range, even when manufacturing extremely small optical formats. Depending upon the complexity of the format, the range may be within a few microns. Other microfabrication techniques which can be used to manufacture optical formats according to this invention include embossing of plastic sheets or the use of UV cure epoxy over master forms. Further, the capillary gap can be laser cut or molded via conventional molding.

Using an optical format according to the present invention, it is possible to perform accurate optical sample analysis on sample volumes in the range of from about 200 nl to about 500 nl, though optical formats may be adapted for use with larger or smaller volumes.

While the present invention has been described with reference to one or more particular embodiments, those skilled in the art will recognize that many changes may be made thereto without departing from the spirit and scope of the present invention. For example, while the present invention has been generally described as directed to medical applications it is to be understood that any optical fluid testing applications might employ the principles of the invention. Each of these embodiments and obvious variations thereof is contemplated as falling within the spirit and scope of the claimed invention, which is set forth in the following claims.

What is claimed is:

1. A format for optical analysis of samples comprising:
  a light input;
  an input light guide in optical communication with said light input;
  an input reflector coupled with said input light guide for forming a portion of an optical communication path, said optical communication path being continuous and closed between said light input and said input reflector;
  an output reflector in optical communication with said input reflector;
  a sample cavity disposed between said input reflector and said output reflector;
  a lancet in communication with said sample cavity;
  an output light guide coupled with said output reflector for forming a portion of said optical communication path; and
  a light output, said optical communication path being continuous and closed between said light output and said output reflector,
  wherein said light input, said input light guide, said input reflector, said sample cavity, said output reflector, said output light guide, and said light output comprise said optical communication path, and wherein each of said input light guide and said output light guide is formed by a respective wall structure to assist in guiding light along said optical communication path, each of said wall structures including a respective first end and a respective second end, said second end of said input light guide being coupled with said input reflector and said second end of said output light guide being coupled with said output reflector for forming respective portions of said optical communication path, said format further comprising a lid disposed approximately parallel to said optical communication path, wherein the format further includes a reagent therein, said lancet being adapted to collect and deposit test material within said sample cavity such that said test material is positioned to interact with said reagent.

2. The format of claim 1 further comprising a venting channel connected to said sample cavity, wherein said lancet is positioned within said venting channel.

3. The format of claim 1 wherein said input light guide defines a first portion of said optical communication path, and wherein said input reflector is disposed at about a 45-degree angle to said first portion of said optical communication path.

4. The format of claim 3 wherein said output light guide defines a second portion of said optical communication path, and wherein said output reflector is disposed at about a 45-degree angle to said second portion of said optical communication path.

5. The format of claim 1 wherein the reagent is disposed within said sample cavity.

6. The format of claim 5 wherein at least a portion of said lid is adjacent said sample cavity and is provided with the reagent thereon.

7. A format for optical analysis of a sample comprising:
  an input light guide being formed by a first wall structure having a first end and a second end, said second end being coupled with an input reflector;
  an output light guide being formed by a second wall structure having a first end and a second end, said second end being coupled with an output reflector; and
  a light transmission segment disposed between said input reflector and said output reflector, said light transmission segment having a sample cavity; and
  a lancet in communication with said sample cavity, said lancet being adapted to collect and deposit test material within said sample cavity,
  wherein said input light guide, said input reflector, said light transmission segment, said output light guide, and said output reflector form an optical communication path, said optical communication path being continuous and closed between said first end of said input light guide and said input reflector and being continuous and closed between said first end of said output light guide and said output reflector.

8. The format of claim 7, wherein said light transmission segment further includes a lid that has a reagent printed thereon, and wherein said lancet is adapted to deposit at least a portion of said test material within said sample cavity such that said at least a portion of said test material is positioned to interact with said reagent printed thereon.

9. The format of claim 7, further comprising a venting channel connected to said sample cavity, wherein said lancet is positioned within said venting channel.

10. The format of claim 7 wherein said first and said second wall structures each include a top surface, a bottom surface, and two opposing side surfaces such that said input light guide and said output light guide are four-sided light guides, a space between said top and said bottom surfaces being a light guide height and said light transmission segment has a top surface, a bottom surface, and two opposing side surfaces, a space between said top and bottom surfaces being a light transmission segment height, said light transmission height being greater than said light guide height.

11. The format of claim 10 wherein said input light guide has a height of approximately 0.04 inches and said light transmission segment has a height of approximately 0.08 inches.

12. The format of claim 7 wherein said input light guide defines a first portion of said optical communication path and said input reflector is disposed at an angle of about 45 degrees from said first portion of said optical communication path.

13. The format of claim 7 wherein said output light guide defines a second portion of said optical communication path and said output reflector is disposed at an angle of about 45 degrees from said second portion of said optical communication path.

14. The format of claim 7, wherein said lancet has a first end for collecting test material and a second end for depositing test material within said sample cavity.

15. The format of claim 8, wherein said sample cavity has a main cavity portion and a venting cavity connected to said main cavity portion, said main cavity portion and said venting cavity being defined by a bottom surface opposing said lid and two opposing staggered side surfaces, said main cavity portion having a width between a portion of said two opposing staggered side surfaces of about 0.007 inches.

16. The format of claim 8, wherein said sample cavity has a main cavity portion and a venting cavity connected to said main cavity portion, said main cavity portion and said venting cavity being defined by a bottom surface opposing said lid and two opposing staggered side surfaces, said venting cavity having a width between a portion of said two opposing staggered side surfaces of about 0.003 inches or narrower.

17. The format of claim 8, wherein said sample cavity has main cavity portion and a venting cavity connected to said main cavity portion, said main cavity portion and said venting cavity being defined by a bottom surface opposing said lid and two opposing staggered side surfaces, said main cavity portion having a width between a first portion of said two opposing staggered side surfaces of about 0.005 inches and said venting cavity having a width between a second portion of said two opposing staggered side surfaces of about 0.002 inches.

18. A format for optical analysis of a sample comprising:
an input light guide coupled with an input reflector;
an output light guide coupled with an output reflector;
a light transmission segment disposed between said input reflector and said output reflector, said light transmission segment so disposed as to allow light to travel through a light transmission path between said input reflector and said output reflector, said light transmission segment further having a sample cavity and a lid, said lid not intersecting said light transmission path; and
a lancet in communication with said sample cavity, said lancet being adapted to collect and deposit test material within said sample cavity,
wherein the format further includes a reagent therein and wherein each of said input light guide and said output light guide is formed by a respective wall structure to assist in guiding the light along an optical communication path, said optical communication path being formed by said input light guide, said input reflector, said light transmission segment, said output light guide, and said output reflector, said optical communication path being continuous and closed between said input light guide and said input reflector and being continuous and closed between said output light guide and said output reflector.

19. The format of claim 18 further comprising a venting channel connected to said sample cavity.

20. The format of claim 18 wherein said input light guide defines a first portion of the optical communication path, and wherein said input reflector is disposed at about a 45-degree angle to said first portion of the optical communication path.

21. The format of claim 1 wherein said input light guide is formed by a first four-sided wall structure and said output light guide is formed by a second four-sided wall structure.

22. The format of claim 18 wherein said input light guide is formed by a first wall structure and said output light guide is formed by a second wall structure.

23. The format of claim 22 wherein said first and said second wall structures each include a top surface, a bottom surface, and two opposing side surfaces such that said input light guide and said output light guide are four-sided light guides.

24. The format of claim 1, wherein said input light guide is substantially straight between its first and second ends and said output light guide is substantially straight between its first and second ends.

25. The format of claim 1, wherein each of said respective wall structures includes a top surface, a bottom surface, and two opposing side surfaces such that said input light guide and said output light guide are four-sided light guides, a space between said top and said bottom surfaces of said input light guide being an input light guide height, a space between said top and said bottom surfaces of said output light guide being an output light guide height, and wherein said sample cavity has a top surface, a bottom surface, and two opposing side surfaces, a space between said top and bottom surfaces of said sample cavity being a sample cavity height, said sample cavity height being greater than said input and said output light guide heights.

* * * * *